US010435366B2

(12) United States Patent
Briault et al.

(10) Patent No.: US 10,435,366 B2
(45) Date of Patent: Oct. 8, 2019

(54) COMPOSITIONS FOR THE TREATMENT OF FRAGILE X SYNDROME

(75) Inventors: Sylvain Briault, Orleans (FR); Olivier Perche, La Chapelle Saint Mesmin (FR)

(73) Assignees: Centre National de la Recherche Scientifique, Paris (FR); Centre Hospitalier Regional d'Orleans, Orleans (FR); University d'Orleans, Orleans (FR)

( * ) Notice: Subject to any disclaimer, the term of this patent is extended or adjusted under 35 U.S.C. 154(b) by 91 days.

(21) Appl. No.: 14/128,154

(22) PCT Filed: Jun. 19, 2012

(86) PCT No.: PCT/IB2012/053089
§ 371 (c)(1),
(2), (4) Date: Mar. 25, 2014

(87) PCT Pub. No.: WO2013/001412
PCT Pub. Date: Jan. 3, 2013

(65) Prior Publication Data
US 2014/0221450 A1 Aug. 7, 2014

(30) Foreign Application Priority Data
Jun. 27, 2011 (EP) .................................. 11171532

(51) Int. Cl.
*A61K 31/404* (2006.01)
*C07D 209/34* (2006.01)

(52) U.S. Cl.
CPC .......... *C07D 209/34* (2013.01); *A61K 31/404* (2013.01)

(58) Field of Classification Search
CPC .................................................. A61K 31/404
See application file for complete search history.

(56) References Cited

U.S. PATENT DOCUMENTS

2002/0045566 A1  4/2002  Gribkoff et al.

FOREIGN PATENT DOCUMENTS

| EP | 2540295 A1 * | 1/2013 | |
| WO | 2005/008249 | 1/2005 | |
| WO | WO 2005/008249 * | 1/2005 | ............. G01N 33/68 |
| WO | WO 2005/008249 A1 * | 1/2005 | ............. G01N 33/68 |
| WO | 2008/060448 A2 | 5/2008 | |
| WO | WO-2008060448 * | 5/2008 | |

OTHER PUBLICATIONS

Brown et al., Autism is Associated with the Fragile-X Syndrome, Journal of Autism and Developmental Disorders, 12(3), 1982.*
Cohen et al., Why are Autism and the Fragile-X Syndrome Associated? Conceptual and Methodological Issues, Am. J. Hum. Genet. 48:195-202, 1991.*
Liao et al., PNAS, 105(40):15281-15286. 2008.*
Goodlin-Jones et al. J Dev Behav Pediatr. Dec. 2004;25(6):392-8.*
Zeier, Fragile X Mental Retardation Protein Replacement Restores Hippocampal Synaptic Function in a Mouse Model of Fragile X Syndrome, Gene Therapy, 16, pp. 1122-1129, 2009.
Rueda, Systematic Review of Pharmacological Treatments in Fragile X Syndrome, BMC Neurology, 9, pp. 53, 2009.
Chang, Identification of Small Molecules Rescuing Fragile X Syndrome Phenotypes in *Drosophila*, Nature Chemical Biology, 4, pp. 256-263, 2008.
Erickson, Aripiprazole in Autism Spectrum Disorders and Fragile X Syndrome, Neurotherapeutics: The Journal of the American Society for Experimental NeuroTherapeutics, 7, pp. 258-263, 2010.
Brown, Fragile X Mental Retardation Protein Controls Gating of the Sodium-Activated Potassium Channel Slack, Nature Neuroscience, 13, pp. 819-821, 2010.
Gross, Fragile X Mental Retardation Protein Regulates Protein Expression and mRNA Translation of the Potassium Channel Kv4.2, The Journal of Neuroscience, 31, pp. 5693-5698, 2011.
Liao, Quantitative Proteomic Analysis of Primary Neurons Reveals Diverse Changes in Synaptic Protein Content in fmr1 Knockout Mice, Proceedings of the National Academy of Sciences of the United States of America, 105, pp. 15281-15286, 2008.
Kaczmarek, Development of Pharmacological Activators of FMRP-Regulated Potassium Channels, http://www.fraxa.org/researchTeam.aspx, retrieved on Nov. 4, 2011.
Brown, Potassium Channel Modulation and Auditory Processing, Hearing Research, 279, pp. 32-42, 2011.
Laumonnier, Association of a Functional Deficit of the BkCa Channel, a Synaptic Regulator of Neuronal Excitability with Autism and Mental Retardation, American Journal of Psychiatry, 163, pp. 1622-1629, 2006.

* cited by examiner

*Primary Examiner* — Rachael E Bredefeld
*Assistant Examiner* — Chris E Simmons
(74) *Attorney, Agent, or Firm* — Morgan, Lewis & Bockius LLP

(57) ABSTRACT

The present invention relates to a composition comprising a maxi-K potassium channel opener the use in the treatment of fragile X syndrome. More specifically the present invention relates to a composition comprising a fluoro-oxindole or a chloro-oxindole for use in the treatment of fragile X syndrome.

8 Claims, 8 Drawing Sheets

COMPOSITIONS FOR THE TREATMENT OF FRAGILE X SYNDROME

Figure 1:
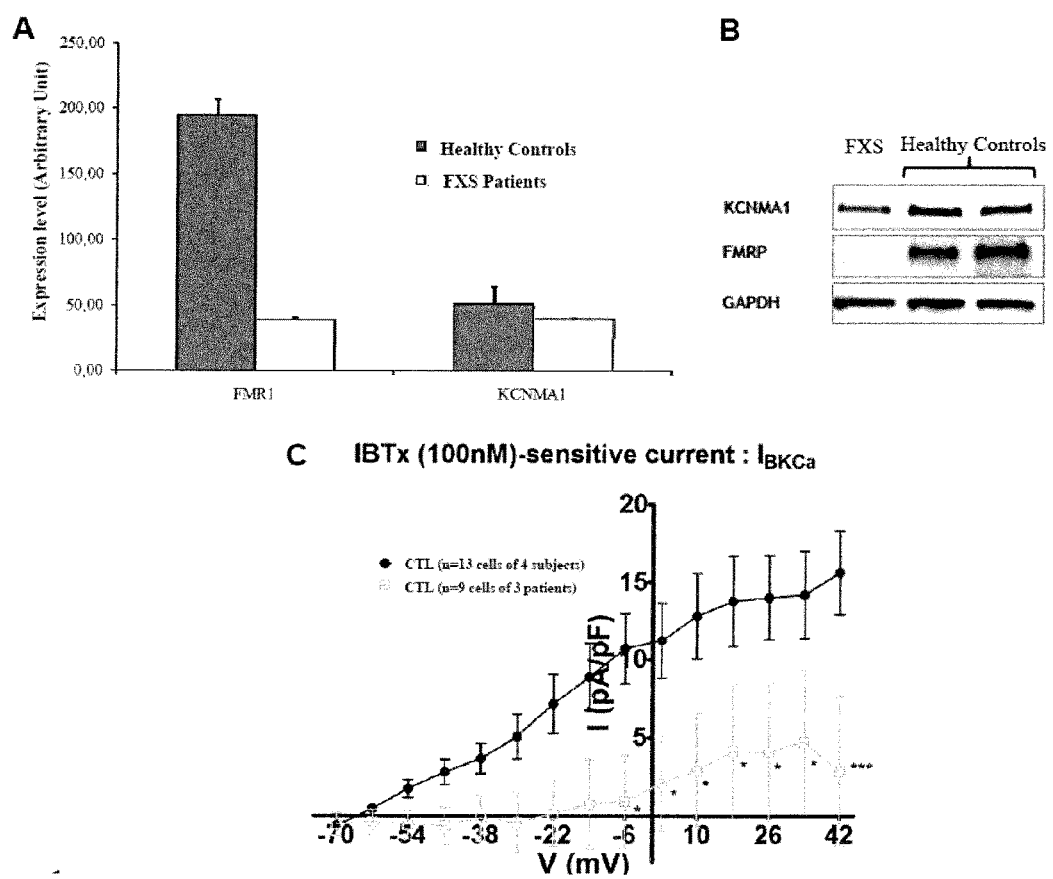

The present invention relates to compositions for the alleviation of neuropsychiatric symptoms and in particular those of Fragile X syndrome.

Neuropsychiatry is the branch of medicine dealing with mental disorders attributable to diseases of the nervous system, this discipline is closely related to neurology but neurology and neuropsychiatry are typically practiced separately. Neurology is a medical specialty dealing with disorders of the nervous system such as pathologies of the central, peripheral and autonomic nervous systems, as well as the connective tissue associated with the nervous system.

The basis of neuropsychiatric conditions can be due to a single gene aberration or a combination of several mutations and/or environmental cues.

An example of a neuropsychiatric disorder caused by a single gene aberration is Fragile X syndrome (FXS). FXS or Martin-Bell syndrome ($ICD_{10}$: Q99.2), is a genetic syndrome which results in a spectrum of characteristic physical and intellectual limitations as well as a number of emotional and behavioral aberrations which range from severe to mild in manifestation. In particular sufferers of FXS can present symptoms of mental disorder upon the autism spectrum as well as epilepsy.

FXS is a Syndromic X-linked Mental deficiency (Hamel and Ropers, 2005) characterized by low IQ (De la Cruz et al., 1985), facial dysmorphia, macro orchidism, making them a clinically recognizable condition. In 5 to 25% of cases mental deficiency can be associated with variable additional symptoms, such as autistic spectrum like behaviors, attention deficit and hyperactivity, childhood seizures and several physical manifestations (Hagerman et al., 2006; Di Bonaventura et al., 2006). The molecular basis of FXS is an abnormal expansion of a COG triplet located at Xq27 in the 5' untranslated region of the FMR1 gene, which leads to a decrease in transcription of the gene. There are three generally accepted states of the chromosome region involved in FXS which relate to the length of the repeated CGG sequence: Normal (29-31 CGG repeats) (not affected by the syndrome), Premutation (55-200 CGG repeats) (not affected by the syndrome), Full Mutation (more than 200 CGG repeats) (affected).

The FMR protein (FMRP) acts as a suppressor of translational activity particularly in neuronal dendrites that control the localization and expression of a set of synaptic specific proteins. It has been proposed that the loss of negative feedback as a consequence of the drop in FMRP production, results in abnormalities in the structure and functioning of the synapses which in turn cause the FXS phenotype.

Aside from intellectual disability, prominent characteristics of FXS include an elongated face, large or protruding ears, flat feet, larger testes (macroorchidism) and low muscle tone. Speech may include cluttered or nervous speech patterns. Behavioral characteristics may include stereotypic movements (e.g., hand-flapping) and atypical social development, particularly shyness, limited eye contact, memory problems and difficulty with facial encoding and recognition. Many individuals with FXS also meet the diagnostic criteria for some autistic-like features. Most females who have the syndrome experience symptoms to a lesser degree because of their second X-chromosome; however, females can develop symptoms just as severe as their male counterparts. While full mutation males tend to present with severe intellectual disability, the symptoms of full mutation females run the gamut of minimally affected to severe intellectual disability, which may explain why females are under diagnosed relative to males, leading to the persistence of the anomaly in the population.

At the present time no medicament has been approved for the treatment of FXS.

FXS is considered an important therapeutic target firstly as it is the most common form of mental retardation attributable to a single gene mutation and also because as the development of drugs to treat neuropsychiatric diseases such as mental retardation or autism is becoming an increasingly important commercial objective, an approach based upon looking at single-gene disorders and the use of these as a window into the field treating of neuropsychiatric diseases such as mental retardation or autism is one of the most attractive development strategies available.

Research in this area has been slow however due to the complex interplay of both genetic and environmental factors in the severity of mental retardation and associated phenotypes. Specifically relating to X-linked forms of mental retardation some one hundred and forty syndromic forms are currently known (Ropers et al., Nature Reviews Genetics 2005) of which some have been shown to have an allelic basis whereas other continue to be uncharacterized. Therefore even though the genetic basis of FXS is known the various biochemical and physiological consequences of this genetic aberration are still being characterized and new types of treatment developed as our knowledge continues to increase.

Workers seeking the means to treat FXS have shown that excessive glutamate accumulates at the synapse of a mouse model of FXS and is responsible for the cognitive deficits seen in this mouse model of FXS (Huber et al. Proc. Natl. Acad. Sci. (2002)). Workers also found that reducing expression of a specific glutamate receptor, mGluR5, reverses these symptoms in the animal model (Dölen et al. Neuron (2007)).

As a consequence of this work mGluR5 inhibitors were developed, notably by Merck & Co Inc and subsequently have been taken into clinical trials.

A second class of drug exemplified by arbaclofen, has also been proposed which stimulates receptors of gamma aminobutyric acid(B) or GABA(B) and thereby dampens glutamate signaling. Clinical trials are also underway to test arbaclofen on children and adults with fragile X syndrome, as well as an open-label trial of children with autism.

Other examples of proposed treatments for FXS are detailed in Table 1 below.

TABLE 1

| Reference | Compound | Effects |
| --- | --- | --- |
| Rueda et al., BMC Neurology 2009 | Folic Acid | Metabolism |
| | Ampakine compound CX516 | AMPA pathway |
| | Dextroamphetamine | Phosphoinositol cycle |
| | Methylphenidate | Dopamine transport inhibitor |
| | L-Acetylcarnithine | Mitochondrial |
| Chang et al., Nature Chemical Biology 2008 | Nipecotic acid | GABA reuptake inhibitor |
| | Creatinine | Metabolism, GABAergic pathway |
| | Ergonovine maleate | Serotonin pathway |
| | Pilocarpine nitrate | Muscarinic agonist |
| | Dienestrol | Sex hormone related |

TABLE 1-continued

| Reference | Compound | Effects |
|---|---|---|
| | Clomiphene citrate | Sex hormone related |
| | GABA | GABAergic pathway |
| | Kojic acid | Tyrosinase inhibitor |
| | Aminobenztropine | Muscarinic agonist |
| | MPEP | mGluR pathway |
| Erickson et al., Neurotherapeutics 2010 | Aripiprazole | Partial dopamine and 5-$HT_{1A}$ agonist and 5-$HT_{2A}$ antagonist |

Several of the proposed treatments for FXS are well characterized drugs such as Dextroamphetamine and Aripiprazole, dietary supplements such as Folic acid or metabolites such as Creatinine, whose pharmacological properties and mode of action are well characterised.

Other workers in the field have proposed alternative treatments for FXS, for instance Zeier et al., (Gene Therapy 2009) proposes a treatment for FXS using gene therapy to replace the faulty endogenous FMRP with a functional version of FMRP. With reference to Brown et al., (Nat. Neurosci. 2010), it would be expected that this increased level of FMRP would activate a specific class of potassium channel, the Slack channel (for sequence like a $Ca^{2+}$-activated $K^+$ channel).

Alternative putative therapeutic targets for treating FXS include the regulation of the expression of the KCND2 gene. KCND2 is another potassium ion channel which forms a voltage-activated A-type potassium ion channel that play a prominent role in the repolarization phase of the action potential. Indeed, many potassium channels seem to be therapeutic targets for the FXS (Lee et al., 2012). Recently, Lee et al. review all potassium channels which could be new ways of treatments, amongst these, Slack, Kv4.2 (KCND2), KV 1.3 were cited.

In Liao et al., (PNAS 2008) a small reduction was observed in the expression level KCNMA1 protein, the alpha subunit of the BKCa channel, in a FMR1 knockout mouse model. Liao et al., were unable to attribute this reduction in the expression of the BKCa alpha subunit to the phenotype of the model as it was just one of 132 proteins (from a starting group of 3880) that showed altered expression. Previously, Hu et al. (2001) and others have demonstrated that BKCa does not modulate synaptic transmission activity.

The Applicants have now discovered a new therapeutic pathway for FXS, the BKCa pathway which has never reported before and have investigated a class of drugs targeting specifically BKCa. This drug can be used to specifically treat the symptoms of FXS and also may be generally applicable to the treatment and alleviation of the symptoms of autism spectrum disorder and/or other classes of neuropsychiatric disorders.

In particular the Applicants have investigated a new therapeutic pathway for FXS, the BKCa pathway, and the effects of agents which act upon this potassium channel as the means to treat the symptoms of two different conditions FXS ($ICD_{10}$: Q99.2) and also more generally those of autism ($ICD_{10}$: F84.0).

Surprisingly the inventors have established that this class of compound can reverse characteristic symptoms associated with FXS and therefore in accordance with a first aspect of the present invention therefore there is provided a composition comprising a maxi-potassium channel opener for use in the treatment of a neuropsychiatric disorder.

In accordance with this aspect of the present invention the neuropsychiatric disorder may in particular show symptoms/behaviors characteristic of autism spectrum disorders.

The autism spectrum, also called autism spectrum disorders (ASD) or autism spectrum conditions (ASC), is a spectrum of neuropsychiatric conditions characterized by widespread abnormalities of social interactions and communication, as well as restricted interests and repetitive behavior.

Specifically in accordance with the present invention there is provided a composition comprising a maxi-K potassium channel opener for use in the treatment of fragile X syndrome.

In accordance with the present invention a Maxi-K channel also known as a BK channel (Big Potassium) or slo1 or BKCa (Big Potassium Calcium) channel or KCNMA1, are ion channels characterized by their large conductance of potassium ions ($K^+$) through cell membranes. These channels are activated (opened) by changes in membrane electrical potential and/or by increases in concentration of intracellular calcium ion ($Ca^{2+}$). Opening of maxi-K channels allows $K^+$ to passively flow through the channel, down the electrochemical gradient. Under typical physiological conditions, this results in an efflux of $K^+$ from the cell, which leads to cell membrane hyper-polarization (a decrease in the electrical potential across the cell membrane) and a decrease in cell excitability (a decrease in the probability that the cell will transmit an action potential).

As with other potassium channels, Maxi-K channels have a tetrameric structure. Each monomer of the channel-forming alpha subunit is the product of the KCNMA1 gene. Modulatory beta subunits (encoded by KCNMB1, KCNMB2, KCNMB3, or KCNMB4) can associate with the tetrameric channel.

In accordance with the present invention a maxi-K channel opener is one which activates maxi-K potassium channels in cells under conditions of high intracellular calcium concentration and does not significantly activate maxi-K potassium channels in cells under low or normal concentrations of intracellular calcium.

As guidance, non-limiting examples of high levels of intracellular calcium are typically considered to be in the high nanomolar (e.g. greater than about 250 or 300 nM) to micromolar range (e.g. about 1 to 10 µM); normal or physiological levels of intracellular calcium are typically considered to be in the range of about 50 nM to 250 nM and low levels of intracellular calcium are typically considered to be in the range of about 5 to 50 nM. A large number of molecules are known to have the ability to open maxi-K channel such as 3-phenyl substituted oxindol derivatives, halo-oxindoles, benzimidazolone (NS 004, NS 1619), benzimidazole, amiodarone (KB 130015), indole carboxylates such as Indole-3-carboxylic acid (CGS 7181, CGS 7184), Arylpyrrole (NS 8), Dihydrosoyasaponin-1 (DHS-1), Terpene, Cerebroside (Baifuzi), Mallotoxine (Rottlerin), Arylquinoline, Aryloxindole, Pimaric acid (PiMa), Dichlorodehydroabietic (diCl-DHAA), Flavonoid (Naringenin, Phloretin), Benzofuroindole (LDD 175), Benzimidazolinone (1-EBIO), Fluoro propionamide [(S)-N-(4-benzoyl-phenyl)-3,3,3-trifluoro-2-hydroxy-2-methyl-propionamide], Unoprostone (and unoprostone isopropyl), Benzothiadiazolamine [6-(trifluoromethoxy)benzothiazol-2-amine], ethylbromide tamoxifen, epoxyeicosatrienoic acid, estradiol-17 beta, Diphenylurea (NS 1608).

One class of potassium channel openers which selectively function on cells having high intracellular calcium concentrations are 3-phenyl substituted oxindol derivatives, as described in U.S. Pat. Nos. 5,565,483 and 5,602,169. Halo-oxindoles such as fluoro-oxindole and chloro-oxindole compounds are within the above-described class and are capable of acting selectively as maxi-K channel openers on cells having high intracellular calcium concentration.

This class of potassium channel opener has been characterized as being sensitive to the intracellular calcium concentration of cells and demonstrated to be most effective under conditions of increased intracellular calcium concentrations, e.g. micro molar range, while being minimally effective or not at all effective under normal physiological intracellular calcium concentrations.

These compounds do not act to an appreciable extent to open maxi-K potassium channels in cells having normal, moderate or low intracellular calcium concentration In WO02/30868, this new class of Potassium channel opener were proposed for use as neuroprotective agents, wherein dysfunction of Potassium channels/over accumulation of calcium is associated with neurons being at risk during neurodegenerative conditions, such as those which occur during acute ischemic stroke.

Maxi-K ion channels are proteins that react to substantial increases in intracellular $Ca^{2+}$ and membrane depolarization by markedly increasing potassium ($K^+$) efflux, rapidly hyperpolarizing the membrane and reducing further voltage-dependent $Ca^{2+}$ influx (V. K. Gribkoff et al., Adv. Pharmacol., 37:319-348 (1997)).

Although clinical trials were undertaken to ascertain the effects of 3-phenyl substituted oxindol derivatives on ischemic stroke victims, no statistically significant effect was observed and therefore studies ceased (B. S. Jensen, CNS Drug Reviews, Vol. 8, No. 4 pp. 353-360 (2002)).

More specifically in accordance with the present invention there is provided a composition comprising a halo-oxindole selected from the group fluoro-oxindole or a chloro-oxindole for use in the treatment of fragile X syndrome.

As indicated above 3-phenyl substituted oxindol derivatives, such as fluoro-oxindole and chloro-oxindole compounds have previously been characterized as maxi-K channel openers.

Suitable fluoro-oxindoles for use according to the present invention include (±)-(5-chloro-2-methoxyphenyl)-1,3-dihydro-3-fluoro-6-(trifluoromethyl)-2H-indol-2-one; (3S)-(+)-(5-chloro-2-methoxyphenyl)-1,3-dihydro-3-fluoro-6-(trifluoromethyl)-2H-indole-2-one and (3S)-(−)-(5-chloro-2-methoxyphenyl)-1,3-dihydro-3-fluoro-6-(trifluoromethyl)-2H-indol-2-one.

A suitable chloro-oxindole for use according to the present invention include ((±)-(5-chloro-2-methoxyphenyl)-1,3-dihydro-3-chloro-6-(trifluoromethyl)-2H-indol-2-one); (3S)-(+)-(5-chloro-2-methoxyphenyl)-1,3-dihydro-3-chloro-6-(trifluoromethyl)-2H-indol-2-one; and (3R)-(−)-(5-chloro-2-methoxyphenyl)-1,3-dihydro-3-chloro-6-(trifluoromethyl)-2H-indol-2-one.

In particular the Applicants have performed a number of experiments using the fluoro-oxindole compound (3S)-(+)-(5-Chloro-2-methoxyphenyl)-1,3-dihydro-3-fluoro-6-(trifluoromethyl)-2H-indol-2-one which is also called BMS-204352 and this compound represents a preferred embodiment of the present invention.

Although the applicants have performed experiments using 3-phenyl substituted oxindol derivatives such as (3S)-(+)-(5-Chloro-2-methoxyphenyl)-1,3-dihydro-3-fluoro-6-(trifluoromethyl)-2H-indol-2-one, given the therapeutic effect is due to the opening of the maxi-K channel, it is clear that all the various substances known to open Potassium channels will have a similarly therapeutic effect.

According to a second aspect of the present invention a method of treating fragile X syndrome in an individual in need thereof, comprising: administering to the individual an effective amount of a maxi-K channel opener, said opener having opener activity on maxi-K potassium channel proteins in neuronal cells having a high intracellular calcium concentration, while having no significant opener activity on maxi-K potassium channel proteins in neuronal cells having normal or low intracellular calcium concentration.

In particular where the maxi-K channel opener is selected from the group consisting of fluoro-oxindole compounds and chloro-oxindole compounds.

Most particularly wherein the fluoro-oxindole compound is selected from the group consisting of (±)-(5-chloro-2-methoxyphenyl)-1,3-dihydro-3-fluoro-6-(trifluoromethyl)-2H-indol-2-one; (3S)-(+)-(5-chloro-2-methoxyphenyl)-1,3-dihydro-3-fluoro-6-(trifluoromethyl)-2H-indole-2-one and (3S)-(−)-(5-chloro-2-methoxyphenyl)-1,3-dihydro-3-fluoro-6-(trifluoromethyl)-2H-indole-2-one.

Alternatively wherein the chloro-oxindole compound is selected from the group consisting of ((±)-(5-chloro-2-methoxyphenyl)-1,3-dihydro-3-chloro-6-(trifluoromethyl)-2H-indol-2-one); (3S)-(+)-(5-chloro-2-methoxyphenyl)-1,3-dihydro-3-chloro-6-(trifluoromethyl)-2,4-indol-2-one; and (3R)-(−)-(5-chloro-2-methoxyphenyl)-1,3-dihydro-3-chloro-6-(trifluoromethyl)-2H-indol-2-one.

For a better understanding of the invention and to show how the same may be carried into effect, there will now be shown by way of example only, specific embodiments, methods and processes according to the present invention with reference to the accompanying drawings in which:

FIG. 1: Analysis of transcription, protein expression and electrophysiological levels of KCNMA1 (BKCa) in human patients with FXS. The expression of the FMR1 gene and KCNMA1 gene is calculated using the expression chip EXON1.0 Affymetrix (Panel A) and verified by quantitative PCR. FXS patients have almost of the FMR1 gene but present a decrease level (20%) of the KCNMA1 mRNA. Quantification of proteins from each of these genes was obtained by Western Blot (Panel B). FXS patients, the inventors observed the absence of FMRP and the inventors also saw a significant decreased of 46% in the amount of the KCNMA1 protein (similar to the 42% decrease in fmr1 ko mice). Analyses of the "electric" activity of the BKCa channel was investigate by electrophysiological study (Patch-clamp). FXS patient present a 50% decreased of the whole cell BKca activity (Panel C).

Figure 2:
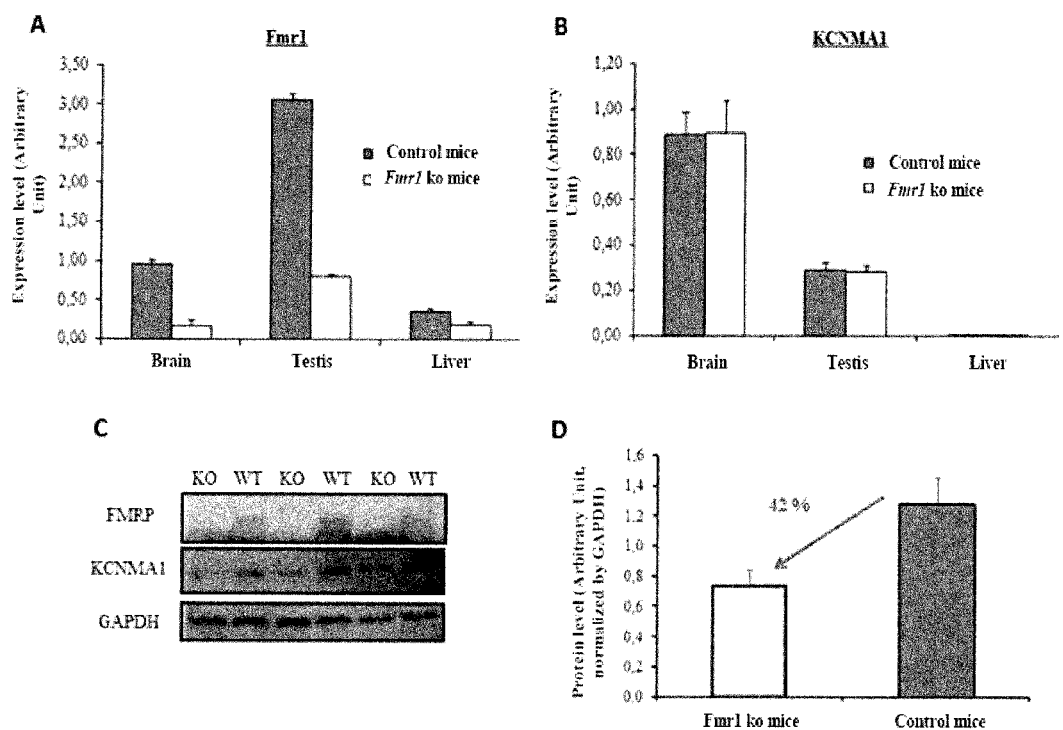

FIG. 2: Analysis of transcriptional and protein levels in mice FMR1 KO and wild type mice. The expression of the FMR1 gene (Panel A) and gene KCNMA1 (Panel B) was studied by quantitative PCR in different organs (brain, testis, liver). FMR1 KO mice exhibit, as expected, virtually no expression of the FMR1 gene but show no abnormalities in the expression of the KCNMA1 gene. Quantification of the FMR1 and KCNMA1 proteins from these genes was obtained by Western blot (Panels C and D respectively). In the brain, FMR1 KO mice, no FMRP was detected and a decreased amount of the KCNMA protein (a 42% reduction compared to wild-type mice (Panel D)) was observed.

Figure 3:
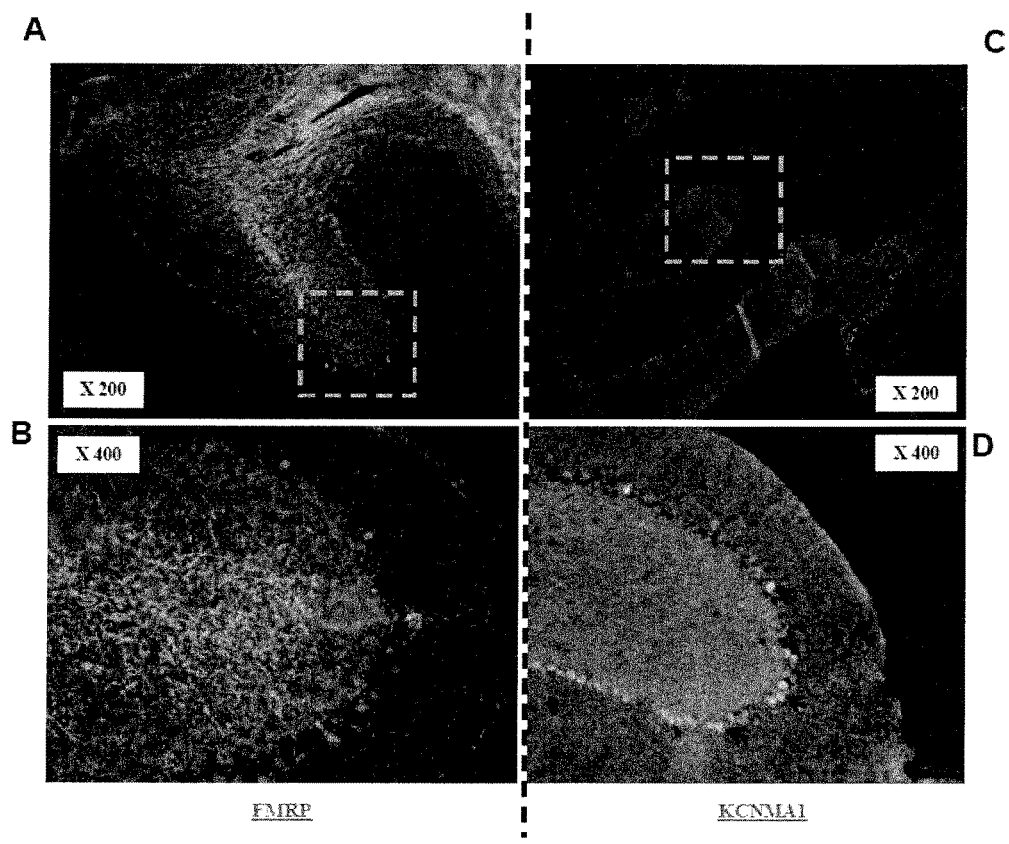

FIG. 3: Immunolocalization of the FMRP protein and the KCNMA1 protein was observed in the cerebellum. The distribution of FMRP [left column A (×200) and B (×400 dotted area)] and the distribution of KCNMA1 [right column C (×200) and D (×400 dotted area)] was carried out in wild type mice. FMRP is present in all the cerebral neurons.

BKCa protein is found in the cerebellum in Purkinje cells (D, arrows). Nuclei were labeled with DAPI.

Figure 4:
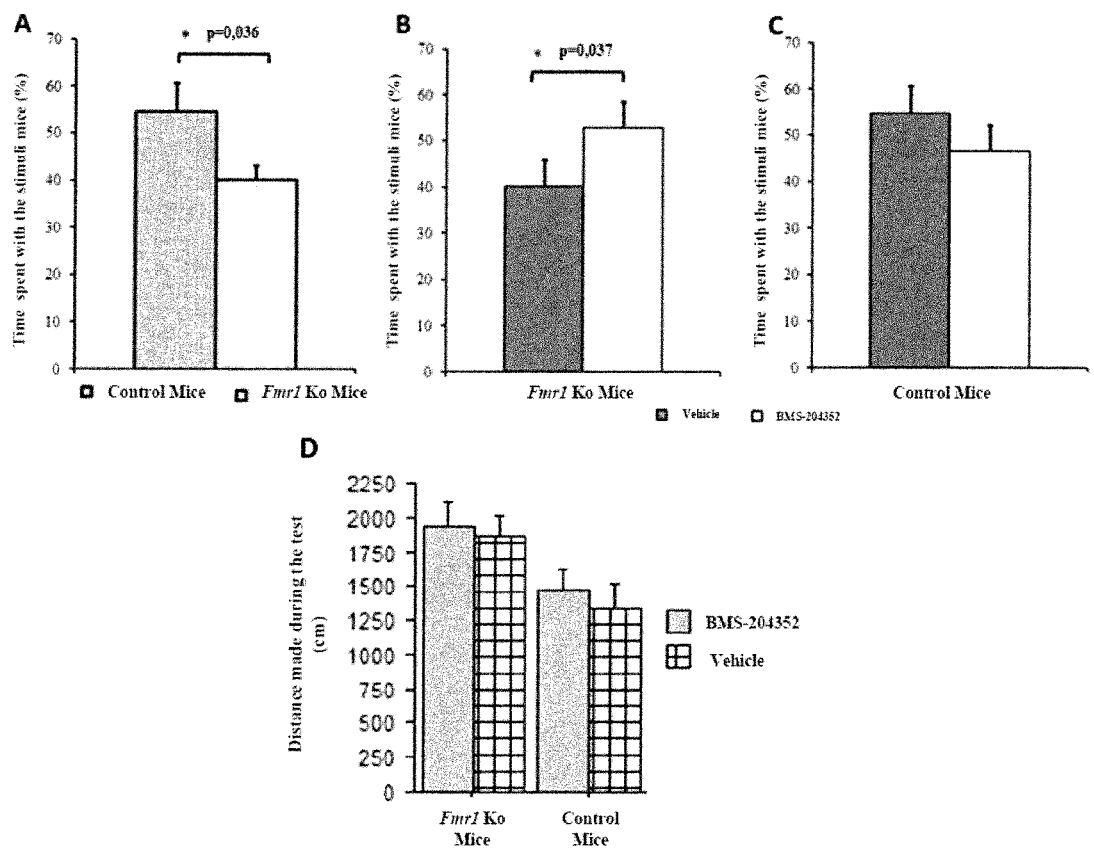

FIG. 4: Analysis of social interaction as per the Crawley test. The social activity of wild type mice and FMR1 KO mice, treated with vehicle or BMS-204352, was studied (n=16 per group). FMR1 KO mice exhibit a lack of social interest significantly (p=0.036) lower than wild type controls (Panel A). An injection of BMS-204352 (2 mg/kg) significantly increased (p=0.037) the social interest of FMR1 KO mice (Panel B). An injection of BMS-204352 (2 mg/kg) did not significantly alter the social activity of wild-type mice (Panel C). The observation of an increased social interest following administration of BMS-204352 to FMR1 KO mice was not due to an increase in locomotor activity (Panel D).

Figure 5:
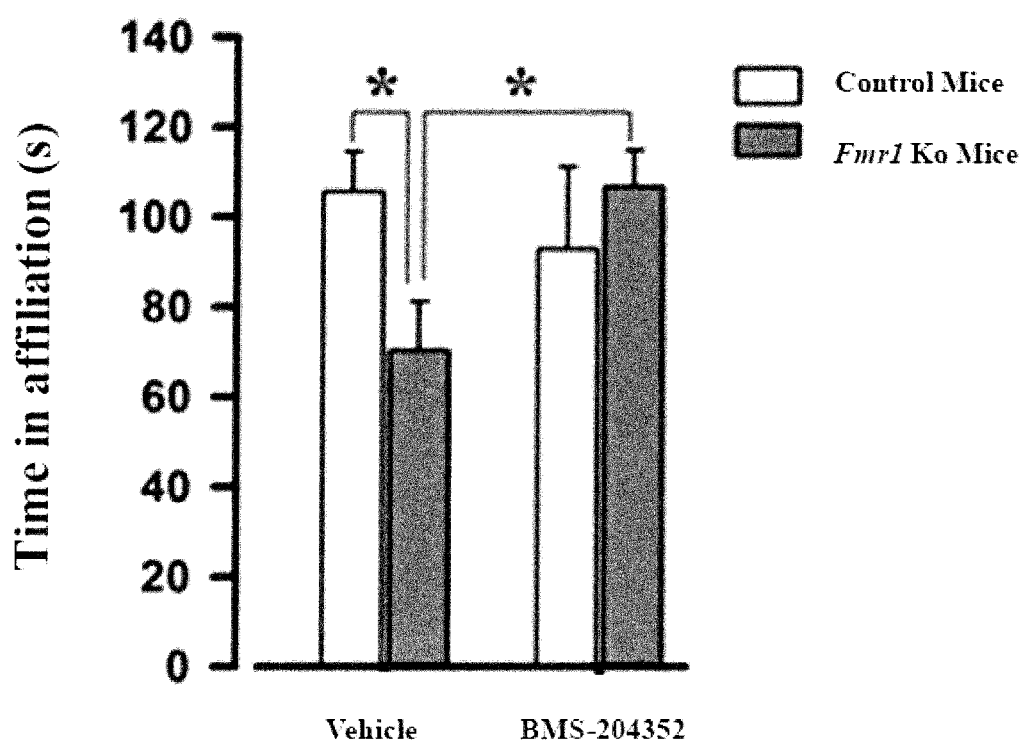

FIG. 5: Analysis of direct social interaction between test mouse (male) with a female. The social activity of wild type mice and FMR1 KO mice, treated with vehicle or BMS-204352, was studied (n=9 per group). FMR1 KO mice have a deficit of social interest in the female compared to control animals, however, an injection of BMS-204352 (2 mg/kg) significantly increased social interaction of FMR1 KO mice and did not have a significant effect upon the wild type control.

Figure 6:
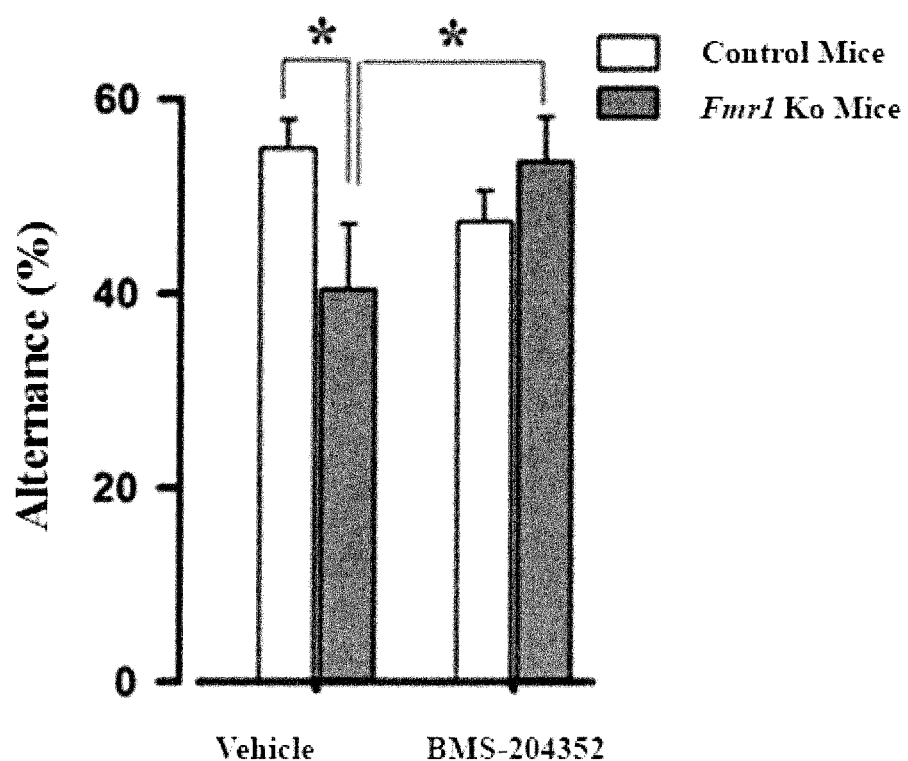

FIG. 6: Analysis of mouse behavior using Y Maze to test for non-social novelty preference. Preference for novelty of wild mice and FMR1 KO, treated with vehicle or BMS-204352, was studied (n=9 per group). FMR1 KO mice show a deficit/lack of interest in the novel environment significantly lower than the wild type mice controls. An injection of BMS-204352 (2 mg/kg) significantly increased the time spent by the FMR1 KO mice in the novel environment.

Figure 7:
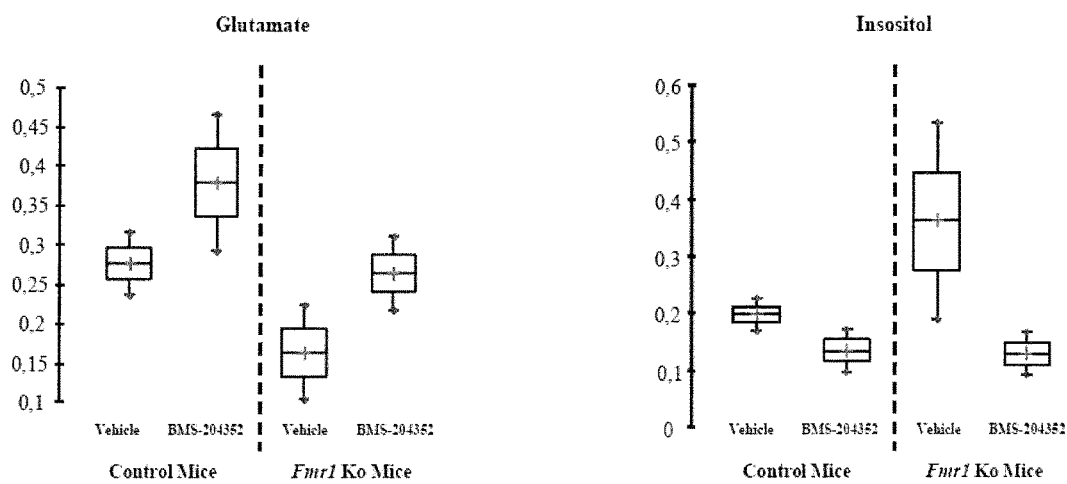

FIG. 7: In vivo cerebral Magnetic Resonance Spectroscopy (MRS). MRS were done in vivo on hippocampus of adult fmr1 ko mice versus controls. The results clearly show a deregulation of several cerebral metabolites. As shown in FIG. 7 (Panel A), Fmr1 ko mice present a significant lower level of glutamate versus controls. This observation is particularly interesting since it confirms the hypothesis of the involvement of a glutamatergic synaptic dysfunction in FXS phenotype. In a second step, the inventors investigated the effect of BMS-204352 on these parameters. Injection of BMS-204352 (single dose in adult mice, as for the behavioral study) induced an increased of the glutamate level which returns to the control level. Once again, it suggests that FXS phenotype is the result of a functional abnormality and not a structural one. As a second observation, a huge increased of inositols (Panel B) level is observed in the ko fmr1 mice. Since cerebral inositol is the marker of astrocyte activation, which are known to collaborate with the neuron for glutamate synthesis, that could say that FXS syndrome is composed by an astrocyte compound. As a confirmation, we have shown that the expression (mRNA) and protein pool of GFAP (Glial fibrillary acidic protein), known to be upregulated in activated astrocyte, are both increased in the fmr1 ko mice. Therefore, astrocyte reactivity seems to contribute to the FXS phenotype. Several other cerebral metabolites were studied and demonstrated that the BMS-204352 rescues the synaptic defects.

Figure 8:
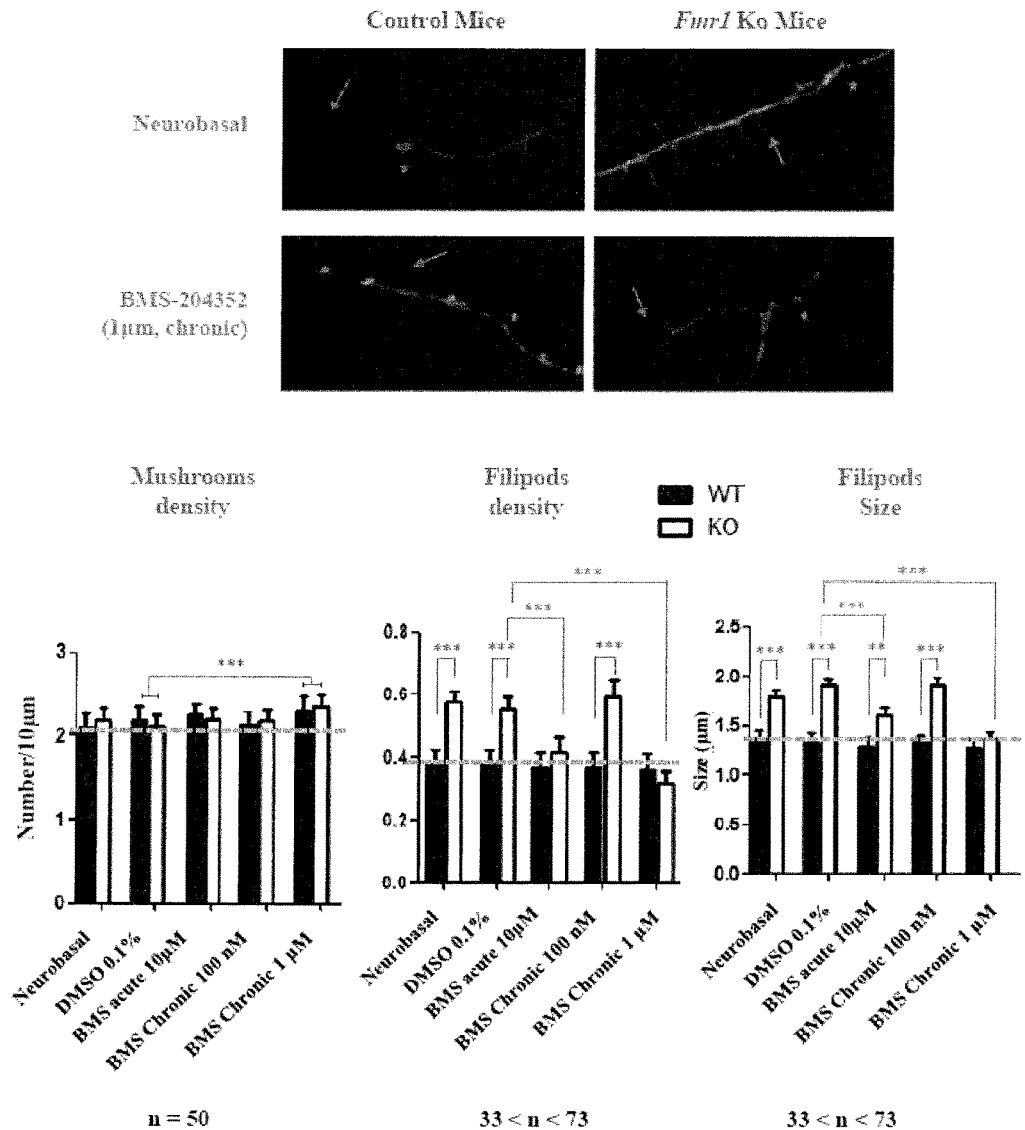

FIG. 8: In vitro dendrite spines matured in the presence of BMS-204352. Primary culture of fmr1 ko neurons demonstrated a lack of maturation of the dendrite spines which are longer, tortuous and thin (Panel A). This observation is consistent with the literature (Irwin et al., 2008; Bilousova et al., 2009). However, chronic addition of BMS-204352 (10 µM) in the media induce the maturation of then dendrite spines (Panel B). These are shorter and larger. This observation demonstrated that BMS-204352 ameliorate the morphological defect of the fmr1 ko, neurons.

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Materials and Methods

Western Blot

Proteins of interest were detected by Western blot. Mice brain or Human Lymphoblastoid cells were homogenized in RIPA buffer [NaCl 0.15M, EDA 1 mM, Tris 10 mM, Nonidet P40 1%, SDS 0.2%] and incubated on ice for 10 before being centrifuged at 11 000 g for 20 min at 4° C. The protein content of the supernatant was quantified using BCA protein assay (Pierce). 60 µg of protein was loaded onto a 12% SDS-polyacrylamide gel. Proteins were then blotted onto a nitrocellulose membrane. After blocking (Tris-buffered saline containing 0.1% Tween 20 and 10% Non fat dry milk, TTBS) the membrane was incubated overnight at 4° C. with anti-FMRP or anti-KCNMA1 (scbt-28739, Santa Cruz biotechnology and APC-021, Alomone, respectively) diluted in TTBS1X at 1:2000. After TTBS1X washes, secondary antibody was incubated 1 hour at 1:4000 (Amersham Biosciences). Immunopositive signals were detected using an ECL plus chemiluminescence detection kit (Amersham Biosciences). Then blots were stripped and reprobed with anti-GAPDH antibody (Abeam). Quantification of immunoreactive bands was done using Image J (Image J Software). On each blot, there were 2 samples per time and three blots were done per antibody.

Expression Assays

RNA Isolation

Frozen brain tissue samples were homogenized in TRIZOL reagent (Invitrogen Life Techonolgies, Carlsbad). Total RNA was extracted using a standard chloroform protocol. RNA integrity was evaluated by using RNA 6000 Nano LabChips on an Applied 2100 Bioanalyzer (Agilent Technologies, Foster City). RNA purity was assessed by the ratio of spectrophotometric absorbance at 260 and 280 nm (A260/280 nm) using NanoDrop ND-1000 (NanoDrop Inc, Wilmington). All chips were prepared according to the manufacturer's instructions. Total RNA degradation was evaluated by reviewing the electropherograms and the quantification of preserved 18S and 28S peaks.

EXON1.0 Affymetrix cDNA was synthesized from RNA total using the GeneChip® WT (Whole Transcript) Sense Target Labelling and Control Reagents kit as described by the manufacturer (Affymetrix). The sense cDNA was then fragmented by UDG (uracil DNA glycosylase) and APE 1 (apurinic/apyrimidic endonuclease 1) and biotin-labelled with TdT (terminal deoxynucleotidyl transferase) using the GeneChip® WT Terminal labelling kit (Affymetrix, Santa Clara, USA). Hybridization was performed using 5 µg of biotinylated target, which was incubated with the GeneChip® Human Exon 1.0 ST array (Affymetrix) at 45° C. for 16-20 hours. Following hybridization, non-specifically bound material was removed by washing and detection of specifically bound target was performed using the GeneChip® Hybridization, Wash and Stain kit, and the GeneChip® Fluidics Station 450 (Affymetrix). The arrays were scanned using the GeneChip® Scanner 3000 7G (Affymetrix) and raw data was extracted from the scanned images and analyzed with the Affymetrix Power Tools software package (Affymetrix). The microarray data has been deposited in the Gene Expression Omnibus Database.

Real Time Quantitative PCR

For each tested gene, commercially available primers and TaqMan probes were used from Agilent Biosystem technologies. PCR was carried out in a 50 µl volume containing 1×PCR buffer Master Mix (Applied Biosystems) and cDNA. For the TaqMan assay, amplification reactions were initially heated to 95° C. for 10 minutes and then subjected to 45 cycles of 94° C. for 15 seconds, 60° C. for 30 seconds, and 72° C. for 30 seconds in Mx3005p (Agilent Biotechnology, Agilent). Fluorescent data were collected during the 72° C. step. The PCR threshold cycle (Ct), which is defined as the fractional cycle number at which the fluorescence reaches 10 times the standard deviation (SD) of the baseline, was determined by the software. Average Ct for duplicate standards and clinical samples was calculated by the software. Standard curve equations were calculated by regression analysis of average Ct versus the log 10 of the standard copy number. The viral copy numbers in the clinical samples were calculated automatically by the data analysis software.

In these assays primer sets KCNMA1: Mm00516078_m1 and FMR1: Mm00484415_m1 were used in mouse studies and KCNMA1: Hs00266938_m1 and FMR1: Hs00924547_m1 were used in human studies, both from Agilent Biosystem technologies.

Behavioral Procedures

Three behavioural tests were made on mice which were 12 weeks of age, the tests were a direct social interaction test with a female, then a three-compartment test for sociability and a spontaneous alternation test in a Y-maze. Two experimental groups (n=10 for both) were studied, the vehicle group (DMSO $\frac{1}{80}^{th}$, Tween 80 $\frac{1}{80}^{th}$, Saline Solution) and the BMS-204352 treated groups (DMSO containing BMS-204352 (2 mg/kg) $\frac{1}{80}^{th}$, Tween 80 $\frac{1}{80}^{th}$, Saline Solution). Administration of each solution was made 30 minutes before the three tests.

Direct Social Interaction with a Female

Apparatus.

Direct social interaction was assessed in a 30×15×22 cm plastic cage with 3 cm of sawdust and a plastic roof with a 17×8 cm central opening.

Procedure.

Experimental and stimulus mice were habituated to the experimental room as before. Each experimental mouse was then introduced into the testing cage and left to habituate for 5 min. An unfamiliar stimulus mouse (NMRI adult female) was then introduced into the testing cage through the roof opening. The testing session lasted 3 min, but was stopped immediately if aggressive episodes occurred. The testing cage was cleansed with water and the sawdust was renewed between sessions. Testing sessions were recorded and videos were analyzed with Observer XT (version 7, Noldus, The Netherlands), taking only the experimental animal into account. One observer who was unaware of the genotype of the animals scored both frequency and duration for each of the following behavioral categories and elements:

Variables Measured

Affiliative behaviors: sniffing the head and the snout of the partner, its anogenital region, or any other part of the body; allogrooming (grooming the partner); traversing the partner's body by crawling over/under from one side to the other.

Nonsocial activities: rearing (standing on the hind limbs sometimes with the forelimbs against the walls of the cage) and digging. Time spent in self-grooming (the animal licks and mouths its own fur) was analyzed separately, since this is sometimes considered to represent repetitive behavior.

Sociability and Preference for Social Novelty in the Three Compartment Test

Apparatus.

The testing apparatus employed here is similar to the one previously described by others (Moy et al., 2004). It consisted of 3 compartments: a central chamber (45×18×25 cm) connected on each side to another compartment (45×20×25 cm) through a small rectangular opening (15×5 cm). The floors and walls (1 cm thick) of all compartments were made of transparent Plexiglas. Each side compartment contained a round stimulus cage (10 cm in diameter, 7 cm high) made of wire mesh (hole size: 0.7×0.7 cm) covered by a plastic roof (5 cm high). A metal weight was attached to the roof in order to keep the stimulus cage stable. Each stimulus cage was placed at a distance of 6 cm from the back wall and 4 cm from the sides. Tracking images from a camera above the center of the apparatus were analyzed with Ethovision (Version 3.1, Noldus Technology, Wageningen, The Netherlands). Procedure. Experimental and stimulus mice (4-week old NMRI male mice) were individually housed in standard polycarbonate cages provided with sawdust, food, and water bottles and left undisturbed in the experimental room for about 10 min before testing began. Each experimental subject was then introduced in the middle of the central compartment and allowed to explore the apparatus for 3 trials of 5 min each:

Trial 1 (habituation): the stimuli cages were empty; basal levels of exploration were assessed.

Trial 2 (sociability): a stimulus mouse was introduced in one of the stimulus cages, while a novel object (a plastic grey cylinder, 6 cm in diameter, 2 cm high) was introduced in the opposite cage (sides were counterbalanced within experimental groups); preferential exploration of the social versus non-social novel stimuli was measured.

Trial 3 (social novelty preference): as trial 2, but the object was exchanged for a novel stimulus mouse; preferential exploration of the novel versus familiar social stimulus was evaluated.

At the end of each trial the experimental animal was confined in the central compartment by means of two Plexiglas magnetic doors for 30 sec. At the end of the third trial the apparatus as well as the object and the stimuli cages were cleansed with water and dried. Variables measured. Exploration of each stimulus was assessed by measuring the time spent in each contact area, a 20622 cm area containing the stimulus cage (see FIG. 1). A percentage score was also computed for the last two trials as follows:

For trial 2: Sociability score=100$T$social stimulus/
($T$social stimulus+$T$non-social stimulus), For trial 3: Social novelty preference
score=100$T$novel social stimulus/($T$novel
social stimulus+$T$familiar social stimulus).

Finally, the total distance moved in the entire apparatus was measured in meters in each trial.

Spontaneous Alternation

Apparatus.

Spontaneous alternation was assessed in a grey, plastic Y-maze, placed on a table 80 cm high and located in the middle of a room containing a variety of extra maze cues. The three arms of the Y-maze were similar in appearance and spaced at 120 cm from each other. Each arm was 42 cm long and 8 cm wide. The entire maze was enclosed by a wall 15 cm high and 0.5 cm thick. Tracking images from a camera above the maze were analyzed with Ethovision.

Procedure.

Mice were habituated to the experimental room as before and then introduced at the end of one of the arms and allowed to explore the maze for 5 min. Allocation of the start arm was counterbalanced within experimental groups. Variables measured. An entry into one of the arms was scored by an observer unaware of the genotype of the animals when all four paws of the animal were placed inside an arm. Thus, if an animal made the following sequence of arm choices: A, B, C, B, A, B, C, A, the total number of alternation opportunities would be six (total entries minus two) and the percentage alternation would be 67% (four out of six).

Magnetic Resonance Spectroscopy

Mice were placed on a custom built device to immobilize their head. They were anesthetized during MR experiment with 1.5% isoflurane and a mixture $O_2/N_2O$ (1:1) with an output of 0.7 L/min. Respiration motion was controlled during all the experiment using a air pillow. Mice body temperature was maintained constant with a warm water circulation. MR spectroscopy was performed on a 7T horizontal ultra shielded refrigerated magnet dedicated to small animal imaging (94/20 USR Bruker Biospec, Wissembourg, France) and equipped with a 950 mT/m gradient set. A Bruker 35 mm inner diameter birdcage coil was used for both $^1H$ transmission and reception. First of all scout images were performed to localzise the voxel of interest (VOI) using a RARE sequence with the following parameters: TR/TE=5 s/56 ms, rare factor=8, FOV size=2*2 cm, matrix size=256*256, slice thickness=1 mm to display (78*78) μm in plane resolution for 5 min duration. Static $B_0$ homogeneity was adjusted with first and second order shims in a (3.5*3.5*3.5) mm voxel centered in the hippocampus with Bruker Fastmap procedure (Gruetter 1993, MRM). The linewidth achieved for tissue water was less than 10 Hz. A PRESS sequence (Point Resolved Spectroscopy) was used to record localized $^1H$ spectra in a cubic (3*3*3) mm voxel placed in fastmap voxel with the following parameters (TR=4 s, TE=16 ms,. 256 scan: 17 min, 2048 points, bandwidth=4000 Hz) with water suppression using VAPOR (VAriable Pulse power and Optimized Relaxation delays) module and outer volume suppression. (Tkac I., MRM 1999). Eddy current compensation and static magnetic field drift correction were applied during spectra acquisition. $^1H$ spectra were collected for WT and KO with or without BMS-204352. Then were analyzed with JMRUI 3.0 software (http://www.mrui.uab.es/mrui/) working in time domain (baseline correction, phasing, zero filling.). AMARES module (JMR1997, 129, 35-43, VanhammeL et al) was used to 9 quantify brain metabolites: N-Acetyl-Aspartate (NAA), glutamate (Glu), glutamine (Gln), γ-aminobutyric-acid (GABA), creatine (Cr), choline (Cho), myo-inositol (Ins), taurine (Tau) and lactate (Lac). Metabolite concentrations obtained in control or ko were compared by pairs using t-test for or Mann-Whitney tests when the distributions were not Gaussian.

Electrophysiology

Whole-cell recordings of K+ currents were acquired in lymphoblastoid cell lines obtained from 3 Fragile-X Syndrome (FXS) patients and 4 age-matched controls individuals. The cells were washed and spun three times and suspended in a physiological saline solution (PSS) composed of the following (in mM): NaCl 137; KCl 4; CaCl2 1.8; MgCl2 1; glucose 10; Hepes buffer 10; pH balanced to 7.4 with NaOH. An aliquot of these cells was then placed in a Petri dish containing 1.5 mL PSS. Petri dishes with cells were then placed on the stage of an Elipse TE-300 Nikon microscope. The cells were suffused with experimental solution via a parallel pipe system lowered into the vicinity of the cells. Cells were intracellularly perfused with a 400 nM free Ca2+ pipette solution (to activate BKCa current) containing (in mM): K-Glutamate 125; KCl 20; CaCl2 0.7; Mg-ATP 1; EGTA 1; Hepes-buffer 10; pH balanced to 7.2 with KOH. Pipette tip resistance ranged between 4 and 6 MΩ Macroscopic K+ currents were generated by progressive 8 mV depolarizing steps (500 msec duration, 5 sec intervals) from a constant holding potential of −70 mV. BKCa current was defined as the outward current inhibited by 100 nM iberiotoxin (IbTx) or 10 μM paxilline (Pax), two selective blockers of BKCa channels. IbTx- and Pax-sensitive currents were expressed as currents density (pA/pF), after estimating the capacitance of each cell. Voltage clamp protocol and data acquisition were controlled with pClamp V 9.0 software (Axon Instruments, Union City, Calif., USA). All experiments were conducted at room temperature. All data are expressed as means±SEM. Statistical comparisons between groups were performed with two-way repeated measures ANOVA with a subsequent Bonferroni post hoc analysis test with Prism V 5.0 (GraphPad). Significance was set at $p<0.05$.

Primary Culture of Neurons

Primary cultures of fmr1ko and wild type mice neurons were prepared from E15 mouse embryos as previously described (Ethell et al. 2001), with modifications. Briefly, after mechanical dissociation, E15 mouse brain cells were plated on coverslips pre-coated with poly-DL-lysinee (0.5 mg/mL in borate buffer). Cells were maintained in Neurobasal medium supplemented with B27 (Invitrogen), 25 1M glutamate, and 1% penicillin-streptomycin, in a humidified 5% CO2/10% O2 incubator at 37_C for 14-17 days. Some hippocampal cultures were labeled with DiI at D14 for dendrite spines observation. All data are expressed as means±SEM. Statistical comparisons between groups were performed with student t test. Significance was set at $p<0.05$.

Results

1. Proteins, mRNA and Electrophysiological Levels of BKCa in Human FXS and Non-FXS Subjects.

The central role of FMRP as regulator of neuronal translation means that any change in its function contributes to disruption of the translation of other proteins and thus via this cascade of disruption alters the protein profile of the cell.

This effect has been clearly shown (Liao L et al, 105: 15281-15286 PNAS (2008)), in a primary culture of neurons from the FMR1 KO mouse (a mouse model of FXS). Among the variations observed, a 50% decrease in the level of the protein KCNMA1 appears to be the most significant. However, this observation has not been verified in humans and therefore the inventors first step was to ascertain the existence of an anomaly in human patients suffering from FXS.

In a first set of experiments, a transcripteomic analysis was performed using DNA microarrays EXON1.0 Affymetrix (GENOTRANS), for the genes FMR1 and Kcnma1, the results were confirmed by RT-PCR (7900 HT, Applied Biotechnology).

Briefly RNA from patients (FXS) and healthy controls was extracted from lymphoblastoid cell lines.

As shown in (FIG. 1A), the expression of FMR1 drops over 95% in patients with FXS, which confirms the phenotype of fragile X syndrome. Moreover, a 20% decrease in mRNA level of the KCNMA1 gene was observed between patients and healthy controls.

Proteomic analysis was also performed by Western blot for FMRP and KCNMA1, using the protein extracts from the same lymphoblastoid cell lines. This analysis, showed a reduction of over 45% of the protein KCNMA1 in FXS patients (FIG. 1B), this reduction was comparable to that observed in FMR1 KO mice by Liao L et al, 105:15281-15286 PNAS (2008). However, the expression profile is different between fmr1 ko mice and human FXS. Electrophysiological analyses were performed on FXS and non-FXS human lymphoblastoid cells and demonstrated a 50% decreased of the BKCa whole cell activity. Therefore, the protein defects are leading to the electric BKCa dysfunction.

In conclusion, therefore the inventors demonstrated an anomaly in KCNMA1 (BKCa) in FXS patients. It is surprising that a KCNMA1 abnormality is found in Fragile X Syndrome and also in a patient with autism (Laumonnier et al., 2006; Patent WO2005/008249). Indeed, these pathologies are strictly different as shown in the DSMIV classification and the ICD10 ladder (Autism: ICD10 F84.0; FRAXA: ICD10 Q99.2). This is of a huge interest since the Fragile X Syndrome is the major form of syndromic mental deficiency with a genetic characterized origin.

Based on the literature, it appears that the modification of the KCNMA1 (BKCa) protein quantity in the FXS syndrome is not relevant. Indeed, Hu and collaborators suggest that modulation of BKCa activity have no effect on the synaptic function, and could not explain the synaptic defects (Hu et al., 2001). Moreover, this un-relevance is confirmed by the absence of description of the BKCa pathway as a therapeutic target in FXS in two recent reviews of Berry-Kravis and Lee (Berry-kravis et al., 2011; Lee et al., 2012). Indeed, in Berry-kravis et al. article, the mGlur1/5, MMP9, GSK3β, GABA and AMPA pathways, and not BKCa one, were described as the only putative therapeutics way of FXS treatments. In the same way, Lee et al. investigate the role of several potassic channels (slack, Kv3.1, etc. . . . ) in the physiopathology of FXS, without any argumentation on BKCa.

The results clearly demonstrated that BKCa is a totally innovative therapeutic target for the FXS. Indeed, it has been demonstrated for the first time that the specific modulation of BKCa channel activity through the BMS-204352 can modify the cerebral function and rescue to "normal" cerebral activity (as evidenced by the Magnetic Resonance Spectroscopy results presented below). These results are totally relevant and characterized the innovation of this work.

The inventors therefore have tested whether that a molecules which can open the BKCa channels such as BMS-204352, may be used as a therapeutic agent for treating human FXS.

2. Study of the Effects of Fluoro-oxindoles on FMR1 KO Mice 2.1 Phenotype Studies The similarities between the behavior observed in FMR1 KO mice and FXS patients, make this mouse strain a good model to study the behavioral features of FXS syndrome (The Dutch-Belgian Fragile X Consortium 1994, and Crusio Bernardet 2006).

FMR1 KO mice are available from the Centre de Neurosciences Integratives et Cognitives—CNRS UMR5228 (S Pietropaolo and W Crusio).

This is strain was obtained by the standard protocol of "The Dutch-Belgian Fragile X Consortium (1994)" by inserting a neomycin cassette in exon 5 of the FMR1 gene by homologous recombination, inactivating the gene.

From a phenotypic point of view, FMR1 KO mice exhibit characteristics of FXS subjects. Thus, male mice have macroorchidism similar to human FXS subjects and also display similar behaviors such as increased levels of anxiety, stereotypical/repeated behaviors and impaired social interaction.

The inventors have also validated this mouse model from a molecular point of view by analyzing the expression of the FMR1 and KCNMA1 genes/gene products.

As shown in FIG. 2, the inventors observed that wild type mice show greatly increased levels of expression of the FMR1 gene in comparison to the FMR1 KO mice, whatever the tissue studied (brain, testis, liver). The residual expression of the FMR1 gene in FMR1 KO mice probably corresponds to a form of "splicing" of the untranslated FMR1 mRNA (Huang et al., 1996) and shows no difference in expression between wild type mice and FMR1 ko mice, which is different in the human condition where KCNMA1 mRNA is deregulated in FXS patients.

In comparison and similarly to that seen in humans, the KCNMA1 gene, is highly expressed in the brain and testis and less in other tissues (FIG. 2B) and shows no difference in expression between wild type mice and FMR1 KO mice. However, the amount of protein KCNMA1 is both decreased (≈45%) in human FXS as in the fmr1 ko mice, validating the theory that FMRP reduction leads to decrease of the translation of KCNMA1 mRNA in both cases. This protein dysfunction leads to a 50% decrease of the whole cell BKCa electric activity (FIG. 1). The amount of protein KCNMA1 produced is however decreased by 42% (FIGS. 2C and D) in FMR1 KO mice brain, validating the theory that FMRP reduction leads to decrease of the translation of KCNMA1 mRNA.

In a parallel series of experiments to better understand the operation of the BKCa channel in connection with FMRP, the inventors studied by immunohistology the distribution in the mouse brain of FMRP and KCNMA1 in wild mice.

From FIG. 3, the BKCa channel is expressed in the cerebellum, in Purkinje cells (right panels C and D, arrows), but also in the cortex, brainstem, and the hippocampus. Furthermore, FMRP is in the brain, but exclusively located inside neurons (FIG. 3, left column).

2.2 Behavioral Studies

To study the therapeutic effect of the molecule BMS-204352, the inventors focused on behavioral parameters that have the greatest effect upon impairment in patients with FXS and mouse FMR1 KO, namely social interactions.

This has been achieved using three behavioral tests previously described by Pietropaolo et al (2011), in collaboration with the authors:

1. Social preference test (the Crawley test),
2. Test for direct social interaction (interaction with a female), and
3. Preference for novelty using a Y maze.

Each of these experiments was performed using adult male mice (3.5 months) with or without intraperitoneal injection of BMS-204352 at 2 mg/kg.

2.2.1 Crawley Test

In this test, the mouse is introduced into an environment in which two other mice are present, these two other mice being called the "stimuli".

One of the stimuli mice is already known to the subject mouse and the second is completely unknown.

The parameter measured is the time spent with each of the two stimuli mice. A wild type mouse would be expected to spend a longer time with the unknown mouse.

The data presented in FIG. 4 shows that:
a. There is a difference of "social interaction" (p=0.036) between wild type mice and untreated mice kb FMR1 (FIG. 4A),
b. That the injection of a single dose of BMS-204352 (2 mg/kg) in adult FMR1 KO mice (3.5 months) significantly improved (p=0.037) its interest in the new mouse (FIG. 4B),
c. Statistical analysis shows no significant difference between wild-type mice treated and untreated (p=0.22) (FIG. 4C),
d. The improvement observed in FMR1 KO mice is not a consequence of an increase in overall locomotive activity (FIG. 4D).

2.2.2 Test of Female Interaction

In this test, a female mouse of another strain, but of the same age is introduced in the environment of the mouse tested.

Affiliative behavior of the mice tested (Sniffing, grooming . . . ) is recorded over the course of a 5 minute period.

The data presented in FIG. 5. show:
1. That there is a difference "direct social interaction" (p=0.04) between untreated wild type mice and untreated FMR1 KO mice, and
2. That the injection of a single dose of BMS 204 352 (2 mg/kg) in adult FMR1 KO mice significantly improves social interaction (p=0.04).

2.2.3 Y Maze Test

This test involved placing the subject animal in a maze which is in the form of a Y, but initially has one closed arm.

After 5 minutes of habituation in the initial maze, the third arm is opened and the time the animal spends in the new arm is recorded.

The data presented in FIG. 6. show:
1. There is a difference of "preference for novelty" (p=0.04) between wild mice and mouse FMR1 KO untreated, and
2. That the injection of a single dose of BMS-204 352 (2 mg/kg) in adult FMR1 KO mice significantly enhances their preference for novelty (p=0.04).

Thus, the injection of a single dose of BMS-204352 to adult male FMR1 KO mice significantly improves their performance in the three different behavioral tests. This result confirms the inventors hypothesis that cognitive and behavioral problems are at least partly related to an abnormality of BKCa and that therefore a therapy which alleviates the effects of the BKCa dysfunction also can alleviate the cognitive and behavioral problems.

In vitro cerebral Magnetic Resonance Spectroscopy (MRS) (FIG. 7) was done on the hippocampus of adult fmr1 ko mice versus controls ones. The results clearly show a deregulation of several cerebral metabolites and confirms the hypothesis of the involvement of a glutamatergic synaptic dysfunction in FXS phenotype. Indeed, the glutamate concentration is significantly reduced in the fmr1 ko mice. Injection of BMS-204352 (single dose in adult mice, as for the behavioral study) induced an increased of the glutamate level which returns to the control level. Therefore, we demonstrated that a part of the FXS phenotype is the result of a functional abnormality and not a structural one, and especially of the glutamatergic synapse. At the contrary of Hu et al. (2001) findings, we demonstrated that the specific targeting of BKCa channel lead to the modulation of the glutamatergic synaptic function. BMS-204352 ameliorates the synaptic function, through its specific action on BKCa.

In vitro dendrite spines maturations were investigate in presence of BMS-204352. Primary culture of fmr1 ko neurons demonstrated an un-maturation of the dendrite spines which is rescued by the chronic addition of BMS-204352 (10 µM) in the media induce the maturation of then dendrite spines. This observation demonstrated that BMS-204352 ameliorate the morphological defect of the fmr1 ko neurons.

Furthermore, the observation of improvement after single-dose treatment of adult mice suggests that behavioral, cerebral function are wholly or partly a consequence of abnormal function and not of a structural change in the BKCa channel.

Based on these results, the inventors could say that, contrary of Hu et al., the modulation of BKCa activity has direct consequences on the glutamatergic synaptic function and the use of BKCa Specific Channel Opener Molecule constitute a good therapeutic way and treatment of the Fragile X Syndrome. Furthermore, two different Channel Opener Molecules were tested (BMS-20452 and 1-EBIO), and both demonstrated a rescued phenotype.

The present invention therefore provides the basis of a potential way to treat FXS.

REFERENCES

1. Liao L, et al. *PNAS*, 105:15281-15286 (2008).
2. Laumonnier F, et al. *Am J Psychiatry*, 163:1622-1629 (2006).
3. Jensen B S, *CNS drug reviews*, 8:353-360 (2002).
4. Gribkoff V K, et al. *Nature medicine* 2001, 7:471-477.
5. Zoute L, et al. *Organic & biomolecular chemistry*, 1:1833-1834 (2003).
6. Hamashima Y, et al, *Journal of the American Chemical Society*, 127:10164-10165 (2005).
7. Sausbier M, et al. *PNAS*, 101:9474-9478 (2004).
8. Bernardet M, et al. *The Scientific World Journal*, 6:1164-1176 (2006).
9. Consorthium TD-BFX: *Cell*, 78:23-33 (1994).
10. Huber K. M. et al. *Proc. Natl. Acad. Sci. U.S.A.* 99, 7746-7750 (2002).
11. Dölen G. et al. *Neuron* 56, 955-962 (2007).
12. V. K. Gribkoff et al., *Adv. Pharmacol.*, 37:319-348 (1997).
13. Ropers, H. H., Hamel, B. C., 2005. Nat Rev Genet. 6, 46-57.
14. de la Cruz, F. F., 1985. Am J Ment Defic. 90, 119-23.
15. Di Bonaventura, et al., 2006 Epileptic Disord. 8, 195-9.
16. Hagerman, R. J., 2006. J Dev Behav Pediatr. 27, 63-74.
17. Ropers et al., Nature Reviews Genetics, 6:46-57 (2005).
18. Rueda et al., BMC Neurology, Vol. 9. No. 1: 53 (2009).
19. Chang et al., Nature Chemical Biology, Vol. 4 No. 4: 256-263 (2008).
20. Erickson et al., Neurotherapeutics, Vol. 7: 258-263 (2010).
21. Zeier et al., Gene Therapy, Vol. 16: 1122-1129 (2009).
22. Brown et al., Nat. Neurosci. Vol. 13(7): 819-821 (2010).
23. Gross et al., Journal of Neuroscience, Vol. 31(15): 5693-5698 (2011).
24. Hu, H., et al., 2001 J. Neurosci. 21, 9585-97.
24. Berry-Kravis, E. et al., 2011. J Neurodev Disord. 3, 193-210.
25. Lee, H. Y et al., 2012. Curr Opin Neurobiol.
26. Pietropaolo et al., PLoS One. 2011; 6(2):e17073.
27. Huang, T et al., 1996. Am J Med. Genet. 64, 252-5.

The invention claimed is:

1. A method of treating fragile X syndrome in a subject in need thereof comprising administering to the subject a therapeutically effective amount of a fluoro-oxindole which activates maxi-K potassium channels in cells having an intracellular calcium ion concentration of between 250 nM and 10 µM and which does not significantly activate maxi-K potassium channels in cells having an intracellular calcium ion concentration of between 5 nM and 250 nM, wherein the fluoro-oxindole is selected from the group consisting of: (±)-(5-chloro-2-methoxyphenyl)-1,3-dihydro-3-fluoro-6-(trifluoromethyl)-2H-indol-2-one; (3S)-(+)-(5-chloro-2-methoxyphenyl)-1,3-dihydro-3-fluoro-6(trifluoromethyl)-2H-indol-2-one; and (3S)-(−)-(5-choro-2-methoxyphenlyl)-1,3-dihydro-3-fluoro-6-(trifluoromethyl)-2H-indol-2-one.

2. The method according to claim 1, wherein the fluoro-oxindole is (±)-(5-chloro-2-methoxyphenyl)-1,3-dihydro-3-fluoro-6-(trifluoromethyl)-2H-indol-2-one.

3. The method according to claim 1, wherein the fluoro-oxindole is (3S)-(+)-(5-chloro-2-methoxyphenyl)-1,3-dihydro-3-fluoro-6-(trifluoromethyl)-2H-indol-2-one.

4. The method according to claim 1, wherein the fluoro-oxindole is (3S)-(−)-(5-chloro-2-methoxyphenyl)-1,3-dihydro-3-fluoro-6-(trifluoromethyl)-2H-indol-2-one.

5. The method according to claim 2, wherein the (±)-(5-chloro-2-methoxyphenyl)-1,3-dihydro-3-fluoro-6-(trifluoromethyl)-2H-indol-2-one is in a pharmaceutical composition.

6. The method according to claim 4, wherein the (3S)-(−)-(5-chloro-2-methoxyphenyl)-1,3-dihydro-3-fluoro-6-(trifluoronnethyl)-2H-indol-2-one is in a pharmaceutical composition.

7. The method according to claim 3, wherein the (3S)-(+)-(5-chloro-2-methoxyphenyl)-1,3-dihydro-3-fluoro-6-(trifluoromethyl)-2H-indol-2-one is in a pharmaceutical composition.

8. The method according to claim 1, where the subject is a human.

* * * * *